United States Patent [19]

Valenzona et al.

[11] 4,258,004
[45] Mar. 24, 1981

[54] AIR FRESHENER

[75] Inventors: Joseph F. Valenzona, Harbor City; Michael Fenstermaker, Lynwood, both of Calif.

[73] Assignee: Orion Industries, Inc., Compton, Calif.

[21] Appl. No.: 62,060

[22] Filed: Jul. 30, 1979

[51] Int. Cl.³ .................. A24F 25/00; A61L 2/00
[52] U.S. Cl. .................. 422/123; 422/5; 239/57; 239/59
[58] Field of Search .................. 422/120, 123, 5; 24/213 CS, 214; 239/57, 58, 59, 60

[56] References Cited

U.S. PATENT DOCUMENTS

| 2,610,879 | 9/1952 | Pope | 24/213 CS |
| 2,681,827 | 6/1954 | Racz | 422/123 |
| 2,873,488 | 2/1959 | Schafer | 422/123 |
| 3,551,963 | 1/1971 | Mosher et al. | 24/213 CS |
| 3,964,684 | 6/1976 | Schimanski | 239/57 |

FOREIGN PATENT DOCUMENTS

| 560143 | 3/1975 | Switzerland | 239/59 |
| 1503304 | 3/1978 | United Kingdom | 422/5 |
| 1514712 | 6/1978 | United Kingdom | 422/123 |

Primary Examiner—S. Leon Bashore
Assistant Examiner—Chris Konkol
Attorney, Agent, or Firm—Fulwider, Patton, Rieber, Lee & Utecht

[57] ABSTRACT

A disk shaped air freshener includes opposed mating trays which define a cavity therebetween and which are engaged for rotation relative to each other. Windows are defined in both of the trays, and openings to the cavity are increased, decreased, or shut entirely by relative rotation of the trays to alter the alignment of the windows. One tray has an axial sleeve and the other has several cantilevered arms which fit through the sleeve and which engage a radial groove in the sleeve to the hold the trays together in relatively rotatable fashion. A scented element is confined within the cavity between the trays and is allowed to provide a freshening scent through openings defined by the aligned windows in the tray. An adhesive pad is centrally located on one of the trays at the axial center of the air freshener.

1 Claim, 3 Drawing Figures

AIR FRESHENER

BACKGROUND OF THE INVENTION

1. Field of the Invention

The present invention relates to air fresheners for use in masking stale odors in rooms and in vehicles.

2. DESCRIPTION OF THE PRIOR ART

In the past, air freshening devices have been used extensively to suppress objectionable odors present in automotive vehicles, closed rooms and other confined areas. Absorbent articles impregnated with scented chemicals are typically located in passenger occupancy areas of automotive vehicles and in closets, store rooms and even larger rooms in residences and commercial establishments to effectively overcome unpleasant odors produced by smoking materials, mildew, dampness, exhaust and hydrocarbon fumes.

Typical scented deodorizers may be packaged within a cloth or paper wrapping and suspended within a vehicle cab, or room of a building. Alternatively, conventional deodorizers may be packaged in rigid walled enclosures. In some cases, such enclosures are formed of relatively rotatable component elements containing apertures movable relative to each other to vary the degree of circulation of ambient air through the enclosure. However, such devices are not readily positionable and movable to selected locations as desired.

Some conventional deodorizers, usually the softer, lighter variety packaged within cloth or paper wrapping, are frequently suspended by a string, or elastic band from a stem of a rearview mirror, from a light bulb pull chain, or from some other convenient elevated support. When a deodorizer pad dangles in this fashion in an automotive vehicle, it often presents a distraction to the vehicle operator. The sporadic movement of the article hanging from the rearview mirror draws the attention of the operator from the road and other traffic conditions and toward the movement of the deodorizer. Furthermore, because a deodorizer located in this fashion is suspended in front of the windshield, it acts as a visual obstruction to the vehicle operator. As a result, conventional automotive vehicle deodorizers subject the vehicle operator and other passengers to unnecessary visual fatigue and are indeed a traffic hazard. Similarly, when suspended from light bulb pull chains or clothes closet hooks, they interfere with a person's normal movement within a room or closet, or occupy space that is better utilized for garment storage.

Alternatively, and particularly in the case of deodorizers which include rigid walled containers, an air freshener case may be placed upon a shelf or other lateral surface. In automotive vehicles, however, such devices frequently fall to the vehicle cab floor as a result of jostling motion of the vehicle. In closets, valuable shelf space is occupied when a container rests upon a shelf, and frequently the container is covered with stored material, and is thereby rendered ineffective.

SUMMARY OF THE INVENTION

The present invention is directed to a deodorizer apparatus which can be placed in virtually any out of the way position in a vehicle cab or room by means of an adhesive pad located on the deodorizer case. Moreover, the degree of circulation through the deodorizer case can be readily adjusted with a slight movement of only one hand. This is particularly advantageous in automotive vehicles where a vehicle operator must maintain a constant grasp of a steering wheel to safely control the travel of the vehicle. Similarly, it is advantageous to be able to adjust the circulation through the deodorizer using a single hand movement when the device is utilized in closet and storage spaces, since a person entering such areas is frequently carrying burdensome articles, and must otherwise deposit these articles in order to adjust air circulation through a conventional deodorizer device.

The portable air freshener of the invention includes a housing with a cavity formed between a pair of opposing relatively rotatable separate concave trays. Both trays have angularly displaceable windows. The trays include a positive fastening mechanism which allows relative rotation between the trays, but prevents axial separation of the trays. A removable scented element is confined within the cavity, and an adhesive member with an exposed adhesive surface is mounted on one of the selected trays at its axial center.

A significant advantage of the construction of the invention is that a positive fastening mechanism is provided which prevents separation of the trays, should the air freshener housing fall to the floor or otherwise be subjected to violent movement. With conventional frictionally engageable housing sections there is no means to prevent separation of the housing components when this occurs, since such conventional devices will frequently come apart upon only moderate impact.

The fastening mechanism employed in the present invention involves a sleeve extending inwardly from one tray, and a plurality of cantilevered deflectable arms extending in an opposite direction from the other tray. To assemble the housing, the arms of one tray are directed through the sleeve of the other while resiliently biased toward each other to a slight degree. When the trays are moved together with their rims adjacent each other, lips at the ends of the arms reach a radial recess in the sleeve and spring outwardly, thereby axially immobilizing the trays relative to each other. Because this fastening mechanism is at the center of the trays, the frictional moment resisting rotation is very small in contrast with the rotational moment applied to the outer rim of one of the trays to effectuate rotational movement. As a consequence, the registration of the windows in the mating trays can be adjusted with one hand by merely rotating one of the trays relative to the other. The frictional forces resisting movement that occur withing the mechanism for fastening the trays together are so slight, that the bond of the adhesive pad holding the air freshener in position against a surface to which it is afixed is not broken.

The invention may be described with greater clarity and particularly by reference to the accompanying drawings.

DESCRIPTION OF THE EMBODIMENT

Figure 2:
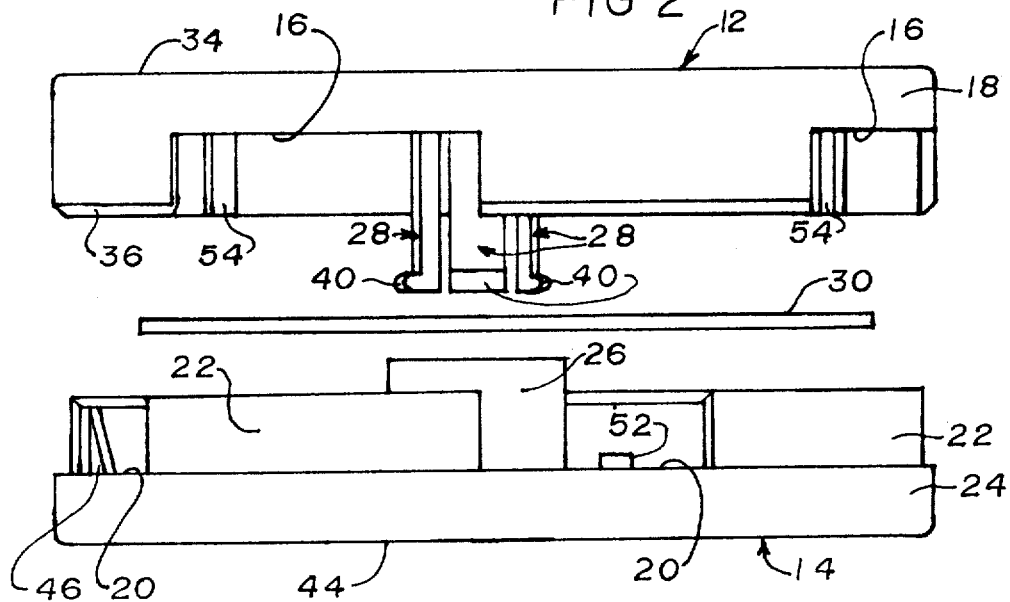
FIG. 2 is an exploded elevational view of the air freshener.
Figure 3:
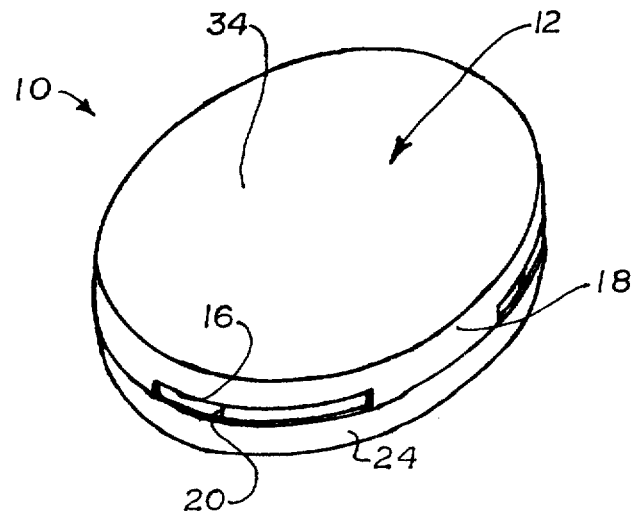
FIG. 3 is a perspective view of the air freshener.

The air freshener of the invention is indicated at 10, and is a generally disk-shaped device slightly less than 73 milimeters in diameter and about 17.5 milimeters thick. The air freshener 10 is formed with a pair of shallow concave mating tray sections 12 and 14, illustrated separately in the exploded view of FIG. 2. Channel shaped windows 16 are defined in the peripheral annular rim 18 of the tray 12 as illustrated in FIG. 2, while similar channel shaped windows 20 are defined in an arcuate, annular partition 22, located immediately adjacent and radially interiorally of the outer peripheral rim 24 of the tray 14. Relative rotation of the trays 12 and 14 brings the windows 16 and 20 into a selected angular orientation relative to each other to increase or decrease air circulation through the air freshener 10.

Figure 1:
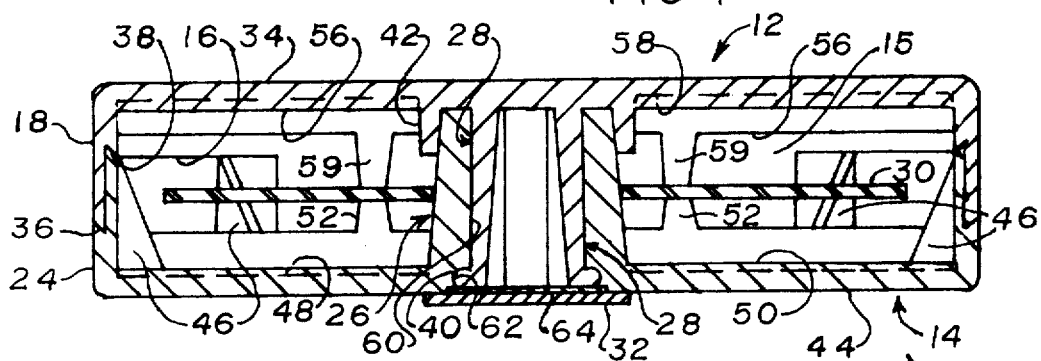
FIG. 1 is a side sectional view of the air freshener of the invention.

The trays 12 and 14 define a cavity 15 therebetween, indicated in FIG. 1. An annular sleeve 26 extends into the cavity 15 from the tray 14 towards the tray 12, while oppositely directed and cooperative cantilevered arms 28 extend from the tray 12 toward the tray 14 to form a fastening mechanism. The fastening mechanism holds the trays 12 and 14 together in the position of FIG. 1 to allow relative rotation therebetween, and prevents axial separation of the trays 12 and 14. A removable annular absorbant pad 30 impregnated with a scented liquid is disposed like a collar upon the outer surface of the sleeve 26 and is confined within the cavity 15 defined between the trays 12 and 14, as depicted in FIG. 1. A thin adhesive disk 32 with an exposed adhesive surface is mounted on the tray 14 at the axial center thereof, as depicted in FIG. 1.

The tray 12 includes an outer laterally expansive exposed disk-shaped surface 34 which extends to a circular annular rim 18 which is turned toward the tray 14. The outer extremity of the rim 18 is formed into an annular beveled surface 36. A corresponding recessed beveled undercut ledge 38 is defined in the interior face of the rim 18 to receive the arcuate partition 22 of the tray 14. Spaced arcuate, channel shaped gaps are defined in the rim 18 from approximately the beveled edge 36 to the ledge 38 to define the arcuate channel-shaped windows 16 therein.

At the interior surface of the tray 12 there are a series of longitudinally extending reinforcing ribs 54 which serve to strengthen the rim 18 of the tray 12. The ribs 54 are located at spaced 90° arcuate intervals near the channel shaped windows 16. Radial ribs 56 are arranged at 90° intervals across the interior roof surface 58 of the laterally expansive disk-shaped portion of the tray 12 for reinforcement. Downwardly extending posts 59 aid in longitudinally immobilizing the annular scented pad 30.

At the axial center of the tray 12 there are four arms 28 held in cantilevered fashion and extending toward the tray 14. The arms 28 are elongated and terminate at their free extremities in radially outwardly directed lips 40. The arms 28 are separated from each other by spaced interstitial gaps, so that they may be deflected radially inwardly toward each other in order to pass through the sleeve 26 of the tray 14. Located outwardly from the base of the arms 28 on the undersurface 58 of the tray 12 there is a short annular guide ring 42 spaced from the arms 28.

The tray 14 also includes an outer expansive disk-shaped surface 44 which is bounded at its periphery by the annular rim 24 directed toward the tray 12. The edge of the rim 24 is undercut in beveled fashion to receive the beveled surface 36 of the rim 18 of the tray 12. The annular partition 22 is defined immediately adjacent to and interiorally of this beveled undercut edge of the rim 24, and likewise terminates at its upper edge in a beveled undercut to mate with the interior ledge 38 on the rim 18 of the tray 12. Spaced gaps 20 are defined in the partition 22 to form arcuate, channel shaped windows.

Triangular shaped upright supporting ribs 46 extend from the floor 48 of the tray 14 to radially reinforce the partition 22 and the circular rim 24 of the tray 14. Elongated radial ribs 50 extend across the floor 48 of the tray 14 at spaced 90 degree intervals to reinforce the disk-spaced expansive portion of the tray 14. Upright posts 52 on each of the radial ribs 50 serve as platforms to aid in holding the annular scented pad 30 in position about the sleeve 26. The upright posts 52 cooperate with the opposing downwardly extending posts 59 to lock the scented pad 30 in position.

The sleeve 26 of the tray 14 includes a cylindrical inner surface 60 which at the end remote from the tray 12 is sculptured to define a quarter round radial groove 62 of configuration adapted to receive the lips 40 of the arms 28 depending from the tray 12. Beyond the groove 62 the surface 60 is further sculptured to provide an axial recess within which a thin disk-shaped cover plate 64 may be positioned. The cover plate 64 frictionally fits into the recess in the disk-like surface 44 of the tray 14, and may bear an embossed indicia of the manufacturer of the air freshener 10.

A thin, flexible, circular pressure sensitive adhesive pad 32 is located immediately outwardly of the cap 64. The pressure sensitive pad 32 includes pressure sensitive adhesive on both sides, so that it may be secured to either the exposed surface 44 of the tray 14, or the exposed surface 34 of the tray 12.

To utilize the air freshener 10, an annular scented pad 30 is first positioned about the sleeve 26 of the tray 14, as indicated in FIG. 2. The pad 30 is then moved toward the floor 48 of the tray 14 until abuts the posts 52, as indicated in FIG. 1. The tray 12 is next moved toward the tray 14. The cantilevered legs 28 are resiliently deflected inwardly toward the axis of the air freshener 10 so that lips 40 clear the interior surface 60 of the sleeve 26. This places the legs 28 in a slightly spring biased condition. The trays 12 and 14 are pushed toward each other with the lips 40 traveling the length of the interior sleeve surface 60 until they reach the sculptured quarter round radial groove 62. The arms 28 thereupon spring outwardly so that the lips 40 engage in the radial groove 62. The cover plate 64 may next be placed in position and is immobilized by the force of friction in the sculptured extremity of the inner surface 60 in the sleeve 26. The adhesive pad 32 may thereupon be placed in position, either as indicated in FIG. 1, or in the opposite surface 34 of the tray 12.

The air freshener 10 is of a diameter such that the rim 18 may be easily grasped with the fingers of one hand of an individual, and rotated either clockwise or counterclockwise to alter the registration of the windows 16 and 20 of the trays 12 and 14 respectively. Increased registration increases the circulation of air flow through the air freshener 10, while only slight registration, or complete misalignment of the windows 16 and 20 will reduce circulation through the air freshener 10 as desired. Because the lips 40 are located near the center of the air freshener 10, they exert only a very slight moment resisting rotation of the trays 12 and 14. This moment is quite small compared to the moment exerted on the rim 18 to adjust the alignment of the windows, and is small enough so that the adhesive seal on the exposed surface of the adhesive disk 32 is not broken when the tray 12 is rotated relative to the tray 14.

The air freshener 10 may be placed in virtually any position, on the underside of dashboards, on the underside of closet shelves, on walls, or in other unobtrusive locations. The air freshener 10 does not require either a horizontal supportive mounted surface, nor does it hang from a string or other suspension device, but rather remains in position by virtue of the adhesive attachment of the adhesive disk 32. Because the alignment of the windows 16 and 20 is so easily performed with one hand of an individual, the air freshener 10 can be readily manipulated and adjusted with considerable convenience to the user.

To change the scented pads 30, the adhesive disk 32 and the cover plate 64 are removed, and the exposed extremities of the cantilevered arms 28 are resiliently moved radially inwardly. The trays 12 and 14 may be readily drawn apart once the lips 40 leave registration with the radial groove 62. The scented pad 30 may then be removed from about the sleeve 26 and replaced with a fresh pad. The trays 12 and 14 may then be re-engaged as previously described.

Undoubtedly, numerous variations and modifications of the invention will become readily apparent to those familiar with air fresheners. Consequently, the scope of the invention should not be construed as limited to the specific embodiment disclosed, but rather is defined in the claims appended hereto.

We claim:

1. A portable air freshener comprising a housing with a cavity formed between first and second opposed relatively rotatable, separable concave trays, said first tray having
a circular annular rim with spaced gaps therein defining channel-shaped windows, the outer edge extremity of said rim being formed into an annular beveled surface, and the inner edge extremity of said rim being formed into a corresponding beveled undercut ledge axially recessed from said outer edge extremity,
radially interiorally disposed axially extending separate positioning posts extending into said cavity,
a plurality of longitudinally separated, resiliently deflectable centrally located cantilevered arms extending axially beyond said rim and arranged in a circular configuration, each arm including a lip at its cantilevered extremity directed radially outwardly from said circular configuration, said second tray comprising
a circular annular rim with an annular partition located radially inwardly therefrom and adjacent therebehind and extending axially beyond said circular rim to reside in sliding contact with the interior surface of said circular rim of said first tray, and spaced gaps are defined in said partition of said second tray to form channel-shaped windows, and the edges of said rim and said partition of said second tray are beveled to respectively reside in mating contact with said beveled surface of said outer edge extremity and said beveled undercut ledge of said circular rim of said first tray, said second tray further comprising separate positioning posts located radially inwardly from said rim thereof in corresponding position relative to said positioning posts of said first tray,
a central annular axial sleeve projecting into said cavity axially beyond said partition and into the inwardly directed surface of the base of which a radial groove is defined, said inner diameter of said sleeve being just less than the span between the extremities of said lips of opposing ones of said arms when said arms are in an unbiased condition, and and said arms are deflectable inwardly to pass through said sleeve so that said lips may be moved into engagement with said radial groove in said base of said sleeve of said second tray,
a removably positioned absorbent pad disposed concentrically about said sleeve and impregnated with a scented liquid and held in said cavity between said opposed positioning posts of said first and second trays,
an external recess defined in said second tray at said base of said sleeve,
a cap removable inserted into said recess at said base of said sleeve and held by friction therein, and
an adhesive member with an exposed pressure sensitive adhesive surface mounted on at least one of said trays at the axial center thereof.

* * * * *